(12) United States Patent
Hassan et al.

(10) Patent No.: US 8,940,347 B2
(45) Date of Patent: Jan. 27, 2015

(54) HIGH SHEAR APPLICATION IN PROCESSING OILS

(75) Inventors: Abbas Hassan, Sugar Land, TX (US); Aziz Hassan, Houston, TX (US); Rayford G. Anthony, College Station, TX (US)

(73) Assignee: H R D Corporation, Houston, TX (US)

( * ) Notice: Subject to any disclaimer, the term of this patent is extended or adjusted under 35 U.S.C. 154(b) by 51 days.

(21) Appl. No.: 13/441,389

(22) Filed: Apr. 6, 2012

(65) Prior Publication Data

US 2012/0282383 A1    Nov. 8, 2012

Related U.S. Application Data

(60) Provisional application No. 61/473,388, filed on Apr. 8, 2011.

(51) Int. Cl.
| | | |
|---|---|---|
| *A23D 9/06* | (2006.01) | |
| *A23L 3/3418* | (2006.01) | |
| *C11B 3/00* | (2006.01) | |
| *B01F 7/00* | (2006.01) | |
| *B01F 13/10* | (2006.01) | |
| *A23D 9/007* | (2006.01) | |
| *A23D 9/04* | (2006.01) | |

(Continued)

(52) U.S. Cl.
CPC ............. *C11B 3/001* (2013.01); *B01F 7/00766* (2013.01); *B01F 13/1016* (2013.01); *A23D 9/007* (2013.01); *A23D 9/04* (2013.01); *C10G 3/00* (2013.01); *C10G 2300/1011* (2013.01); *C10G 2300/1014* (2013.01); *C10G 2300/1018* (2013.01)
USPC ............................. 426/312; 426/417; 261/37

(58) Field of Classification Search
None
See application file for complete search history.

(56) References Cited

U.S. PATENT DOCUMENTS 3,637,402 A * 1/1972 Reid et al. ..................... 426/417
3,758,532 A    9/1973 Gibble (Continued)

FOREIGN PATENT DOCUMENTS

CN      101611120       12/2009
NL      EP 0285198    *  5/1988

(Continued)

OTHER PUBLICATIONS

Gunstone, F. 1983. Lipids in Foods: Chemistry, Biochemistry and Technology. Pergamon Press Ltd., New York. p. 149-150.*

(Continued)

*Primary Examiner* — Carolyn Paden
(74) *Attorney, Agent, or Firm* — Timothy S. Westby; Porter Hedges, LLP (57) ABSTRACT

Herein disclosed is a method of processing oil, comprising providing a high shear device comprising at least one rotor and at least one complementarily-shaped stator configured to mix a gas with a liquid; contacting a gas with an oil in the high shear device, wherein the gas is an inert gas or a reactive gas; and forming a product, wherein the product is a solution, a dispersion, or combination thereof. Herein also disclosed is a high shear system for processing oil, comprising; at least one high shear device, having an inlet and at least one rotor and at least one complementarily-shaped stator configured to mix a gas with a liquid; a gas source fluidly connected to the inlet; an oil source fluidly connected to the inlet; and a pump positioned upstream of a high shear device, the pump in fluid connection with the inlet and the oil source.

15 Claims, 7 Drawing Sheets

(51) Int. Cl.
*C10G 3/00* (2006.01)
*B01D 47/00* (2006.01)

(56) References Cited

U.S. PATENT DOCUMENTS

| | | | |
|---|---|---|---|
| 3,887,167 A | 6/1975 | Irwin | |
| 3,988,329 A | 10/1976 | Zucker | |
| 4,816,189 A | 3/1989 | Rothbart | |
| 4,840,810 A * | 6/1989 | Bodor et al. | 426/312 |
| 4,844,928 A * | 7/1989 | van Heteren et al. | 426/312 |
| 5,298,271 A * | 3/1994 | Takashina et al. | 426/312 |
| 5,470,598 A * | 11/1995 | Scavone | 426/607 |
| 5,538,191 A | 7/1996 | Holl | |
| 5,877,350 A | 3/1999 | Langer et al. | |
| 6,368,366 B1 | 4/2002 | Langer et al. | |
| 6,368,367 B1 | 4/2002 | Langer et al. | |
| 6,383,237 B1 | 5/2002 | Langer et al. | |
| 6,517,884 B1 * | 2/2003 | Bauer-Plank et al. | 426/604 |
| 6,530,964 B2 | 3/2003 | Langer et al. | |
| 6,579,557 B1 * | 6/2003 | Benjamins et al. | 426/603 |
| 6,589,587 B1 * | 7/2003 | Benjamins et al. | 426/603 |
| 6,742,774 B2 | 6/2004 | Holl | |
| 6,863,915 B2 * | 3/2005 | Huxel | 426/312 |
| 7,910,758 B2 * | 3/2011 | Hassan et al. | 554/169 |
| 8,147,895 B2 * | 4/2012 | Barendse et al. | 426/602 |
| 2003/0043690 A1 | 3/2003 | Holl | |
| 2004/0052158 A1 | 3/2004 | Holl | |
| 2005/0033069 A1 | 2/2005 | Holl et al. | |
| 2006/0245991 A1 | 11/2006 | Holl et al. | |
| 2008/0161588 A1 * | 7/2008 | Hassan et al. | 554/169 |
| 2009/0036694 A1 | 2/2009 | Hassan et al. | |
| 2009/0306419 A1 | 12/2009 | Myong et al. | |
| 2010/0199545 A1 | 8/2010 | Hassan et al. | |
| 2010/0294699 A1 | 11/2010 | Hassan et al. | |
| 2011/0003370 A1 | 1/2011 | Gordon et al. | |
| 2012/0111769 A1 * | 5/2012 | Hassan et al. | 208/196 |
| 2013/0266703 A1 * | 10/2013 | Hassan et al. | 426/313 |

FOREIGN PATENT DOCUMENTS

| | | |
|---|---|---|
| WO | 02064708 A2 | 8/2002 |
| WO | 2010090811 | 8/2010 |

OTHER PUBLICATIONS

Chattopadhyay et al., "Understanding Mechanical Energy Driven Nonequilibrium Processing: Some Results, Eleventh International Conference on Rapidly Quenched and Metastable Materials," A Material Science and Engineering, vol. 375-377, dated Jul. 15, 2004, pp. 72-77 (9 pgs.).
IKA-DRS Reactors website http://www.ikausa.com/dr.him, on Sep. 8, 2010 (2 pgs.).
IKA, "Introduction to IKA's Three Stage Dispax Reactor," Retrieved from <http://www.ikausa.com/pdfs/process/dr%202000-Homogenizing-Dispersing-Suspending-Emulsifying.pdf> on Aug. 22, 2012 (12 pgs.).
Office Action dated Jun. 25, 2009 for U.S. Appl. No. 12/142,447 (10 pgs.).
Office Action dated Jan. 7, 2010 for U.S. Appl. No. 12/142,447 (6 pgs.).
Office Action dated May 13, 2010 for U.S. Appl. No. 12/142,447 (5 pgs.).
Office Action dated Feb. 4, 2010 for U.S. Appl. No. 12/492,721 (5 pgs.).
Office Action dated Feb. 18, 2010 for U.S. Appl. No. 12/635,433 (6 pgs.).
Office Action dated Feb. 18, 2010 for U.S. Appl. No. 12/635,454 (6 pgs.).
Office Action dated May 14, 2010 for U.S. Appl. No. 12/137,441 (15 pgs.).
Office Action dated Feb. 19, 2010 for U.S. Appl. No. 12/144,459 (10 pgs.).
Office Action dated Sep. 2, 2009 for U.S. Appl. No. 12/142,433 (11 pgs.).
Office Action dated Jan. 29, 2010 for U.S. Appl. No. 12/142,433 (8 pgs.).
Office Action dated May 24, 2011 for U.S. Appl. No. 12/142,433 (10 pgs.).
Office Action dated Apr. 30, 2010 for U.S. Appl. No. 12/141,191 (12 pgs.).
Office Action dated Oct. 27, 2009 for U.S. Appl. No. 12/142,120 (15 pgs.).
Office Action dated May 5, 2010 for U.S. Appl. No. 12/571,537 (12 pgs.).
Office Action dated Feb. 24, 2011 for U.S. Appl. No. 12/796,358 (13 pgs.).
Office Action dated Feb. 29, 2012 for U.S. Appl. No. 12/146,733 (8 pgs.).
Office Action dated Jun. 3, 2011 for U.S. Appl. No. 12/568,155 (11 pgs.).
Office Action dated Jun. 2, 2011 for U.S. Appl. No. 12/427,286 (12 pgs.).
Office Action dated Jun. 3, 2011 for U.S. Appl. No. 12/568,280 (16 pgs.).
Search Report and Written Opinion dated Aug. 22, 2013 for corresponding International Application No. PCT/US2012/032517 (12 pgs.).
Palanisamy, et a. "An Effective Ostrich Oil Bleaching Technique Using Peroxide Value as an Indicator" Molecules (2011) vol. 16 (5709-5719).
Gogate, et al. "Cavitation: A technology on the horizon," Current Science 91 (No. 1) 35-46 (2006).
IKA—Rotor Stator Generators—2003 Process Catalog (38 pgs.).
International Preliminary Report on Patentability dated Oct. 17, 2013 for corresponding International Application No. PCT/US2012/032517 (8 pgs.).
European Examination Report dated Aug. 6, 2014 for corresponding European Application No. 12864927.4-1361 (6 pgs.).
Canadian Office Action dated Oct. 28, 2014 for corresponding Canadian Application No. 2,828,892(4 pgs.).
Chinese Office Action dated Nov. 29, 2014 for corresponding Chinese Application No. 201280016913.1 (9 pgs.).

* cited by examiner

HIGH SHEAR APPLICATION IN PROCESSING OILS

CROSS-REFERENCE TO RELATED APPLICATIONS

This application claims the benefit under 35 U.S.C. §119 (e) of U.S. Provisional Patent Application Ser. No. 61/473, 388 filed Apr. 8, 2011. The disclosure of said application is hereby incorporated herein by reference.

STATEMENT REGARDING FEDERALLY SPONSORED RESEARCH OR DEVELOPMENT

Not applicable.

BACKGROUND

Field of the Invention

This invention relates to processing oil; specifically it relates to processing oil utilizing a high shear device.

Background of the Invention

Generally speaking, oil includes vegetable oils, volatile essential oils, petrochemical oils, and synthetic oils. Alternatively oils may be categorized into organic oils and mineral oils. There is a wide variety of organic oils, produced from/by plants, animals, and other organisms through natural metabolic processes. Organic oils mainly contain lipids and may also contain other compounds such as proteins, waxes and alkaloids. Mineral oils, on the other hand, are produced from crude oil, or petroleum, and its refined components, collectively termed petrochemicals. They are crucial resources in the today's economy. Crude oil originates from ancient fossilized organic materials, which geochemical processes convert into oil. Mineral oil may also refer to several specific distillates of crude oil.

Vegetable fats and oils are lipid materials derived from plants. Physically, oils are liquid at room temperature, and fats are solid. Chemically, both fats and oils are composed of triglycerides. They may be extracted from different parts of plants; but they are extracted primarily from plant seeds. A common process in producing a vegetable oil comprises extraction, degumming, refining (chemical and physical), hydrogenation and deodorization. A common problem with vegetable oils (e.g., as cooking oils) is rancidification or degradation caused by oxidation, which may cause undesirable odors and flavors.

Ostrich oil has been used extensively in the cosmetic and pharmaceutical industries. However, rancidity causes undesirable chemical changes in flavor, color, odor and nutritional value. Therefore, there is a need to further develop methods and systems in oil processing, for example, to stabilize an oil and/or to improve its quality.

SUMMARY

Herein disclosed is a method of processing oil. The method comprises providing a high shear device comprising at least one rotor and at least one complementarily-shaped stator configured to mix a gas with a liquid; contacting a gas with an oil in the high shear device, wherein the gas is an inert gas or a reactive gas; and forming a product, wherein the product is a solution, a dispersion, or combination thereof.

In some embodiments, the solution is saturated or supersaturated with the gas. In some embodiments, the solution is no less than 5% supersaturated with the gas. In some embodiments, the dispersion comprises gas bubbles with a mean diameter of less than 50 μm.

In some embodiments, the gas comprises nitrogen, a noble gas, carbon dioxide, hydrogen, or hydrogen sulfide. In some embodiments, the oil comprises vegetable oil. In some embodiments, the oil comprises edible oil or inedible oil. In some embodiments, the oil comprises soybean oil. In some embodiments, the oil comprises ostrich oil.

In some embodiments, the oil is selected from the group consisting of soybean oil, sunflower oil, coconut oil, corn oil, cottonseed oil, olive oil, palm oil, peanut oil (ground nut oil), rapeseed oil (including canola oil), safflower oil, sesame oil, hazelnut oil, almond oil, cashew oil, macadamia oil, mongongo nut oil (or manketti oil), pecan oil, pistachio oil, sacha inchi (plukenetia volubilis) oil, walnut oil, watermelon seed oil, bottle gourd oil, buffalo gourd oil, butternut squash seed oil, pumpkin seed oil, acai oil, blackcurrant seed oil, borage seed oil, evening primrose oil, carob seed pods, amaranth oil, apricot oil, apple seed oil, argan oil, artichoke oil, avocado oil, babassu oil, ben oil, borneo tallow nut oil, cape chestnut oil (Yangu oil), carob pod oil (algaroba oil), cassia oil, cocoa butter, cocklebur oil, cohune oil, coriander seed oil, dika oil, false flax oil, flax seed oil, grape seed oil, hemp oil, kapok seed oil, kenaf seed oil, lallemantia oil, manila oil, meadowfoam seed oil, mustard oil, nutmeg butter, okra seed oil, papaya seed oil, perilla seed oil, pequi oil, pine nut oil, prune kernel oil, quinoa oil, ramtil oil, rice bran oil, royle oil, tea seed oil (camellia oil), thistle oil, tigernut oil (or nut-sedge oil), tomato seed oil, wheat germ oil, castor oil, coconut oil (copra oil), corn oil, cottonseed oil, false flax oil, hemp oil, mustard oil, palm oil, peanut oil, radish oil, rapeseed oil, ramtil oil, rice bran oil, safflower oil, salicornia oil, tigernut oil, tung oil, algae oil, copaiba, honge oil, jatropha oil, jojoba oil, milk bush, petroleum nut oil, walnut oil, dammar oil, linseed oil, poppyseed oil, stillingia oil (Chinese vegetable tallow oil), vernonia oil, lemon oil, orange oil, grapefruit seed oil, amur cork tree fruit oil, balanos oil, bladderpod oil, brucea javanica oil, burdock oil (bur oil), candlenut oil, carrot seed oil, castor oil, chaulmoogra oil, crambe oil, cuphea oil, illipe butter, jojoba oil, mango oil, mowrah butter, neem oil, ojon oil, rose hip seed oil, rubber seed oil, sea buckthorn oil, shea butter, snowball seed oil (viburnum oil), tall oil, tamanu oil, tonka bean oil (Cumaru oil), and combinations thereof.

In some embodiments, the method comprises utilizing the method of this disclosure and an existing oil processing method. In some embodiments, the method of this disclosure is applied between the steps of refining oil and bleaching oil. In some embodiments, the method of this disclosure is applied after deodorizing oil. In some embodiments, the method of this disclosure is applied more than once.

Also disclosed herein is a high shear system for processing oil, the system comprising: at least one high shear device, having an inlet and at least one rotor and at least one complementarily-shaped stator configured to mix a gas with a liquid; a gas source fluidly connected to the inlet; an oil source fluidly connected to the inlet; and a pump positioned upstream of the at least one high shear device, the pump in fluid connection with the inlet and the oil source.

In some embodiments, the gas source is configured to provide nitrogen, a noble gas, carbon dioxide, hydrogen, or hydrogen sulfide. In some embodiments, the system further comprises at least one heat exchanger, wherein the heat exchanger is configured to preheat the oil. In some embodiments, the high shear device is configured to form a product of the gas in the oil, wherein the product is a solution, a dispersion, or combination thereof.

In some embodiments, the system further comprises an oil extraction unit. In some embodiments, the system further comprises a degumming unit. In some embodiments, the system further comprises a neutralization unit. In some embodiments, the system further comprises a bleaching unit. In some embodiments, the system further comprises a hydrogenation unit. In some embodiments, the system further comprises a deodorization unit. In some embodiments, the system further comprises a steam refining unit.

These and other embodiments, features and advantages will be apparent in the following detailed description and drawings.

BRIEF DESCRIPTION OF THE DRAWINGS

For a more detailed description of the preferred embodiment of the present invention, reference will now be made to the accompanying drawings, wherein.

DETAILED DESCRIPTION

Overview. In this disclosure, a method of processing oil is described. In this disclosure, oil refers to organic oils unless specified otherwise. Also, vegetable oil is often used in this disclosure as a representative of organic oils. It is easily appreciated by one skilled in the art that the high shear processing method and system as described herein for vegetable oil are also applicable to other oils. For ease of reference, the term "vegetable oil" as used in this disclosure includes both vegetable oils and fats. It is easily understood by one skilled in the art that the method for processing a vegetable oil (liquid phase) is applicable for processing a vegetable fat (solid phase) by adjusting the temperature of the process so that a solid-phase vegetable fat is in the form of a liquid-phase vegetable oil.

This method comprises mixing a gas (e.g., nitrogen) with an oil in a high shear device to form a product of the gas in the oil, wherein the product is a solution, a dispersion, or combination thereof. For ease of reference, the oil-gas product may also be referred to as dispersion/solution throughout this disclosure. The oil-gas product after high shear processing is more resistant to oxidation and is therefore more stable. Furthermore, the oil-gas product is able to retain more valuable compounds, e.g., Omega-3 fatty acids.

Without wishing to be limited by a theory, it is believed that the high shear action is able to supersaturate the gas in the oil so that the amount of oxygen present with the vegetable oil is reduced, thus decreasing the oxidation acted upon the oil. Furthermore, on the molecular level, the gas molecules provide an internal blanketing effect on the unsaturated triglycerides so that oxidation/rancidification is further prevented or retarded.

Super-saturation. In some embodiments, the application of high shear enables the oil to be super-saturated with the gas (compared to when high shear is not applied) and produces a stable solution. In this disclosure, super saturation means that the solution (or the solvent) contains an amount of solute more than the amount of solute at equilibrium state when compared at the same condition. The percentage of the excess amount of solute is a measure of the degree of super saturation of the solution.

Figure 4:
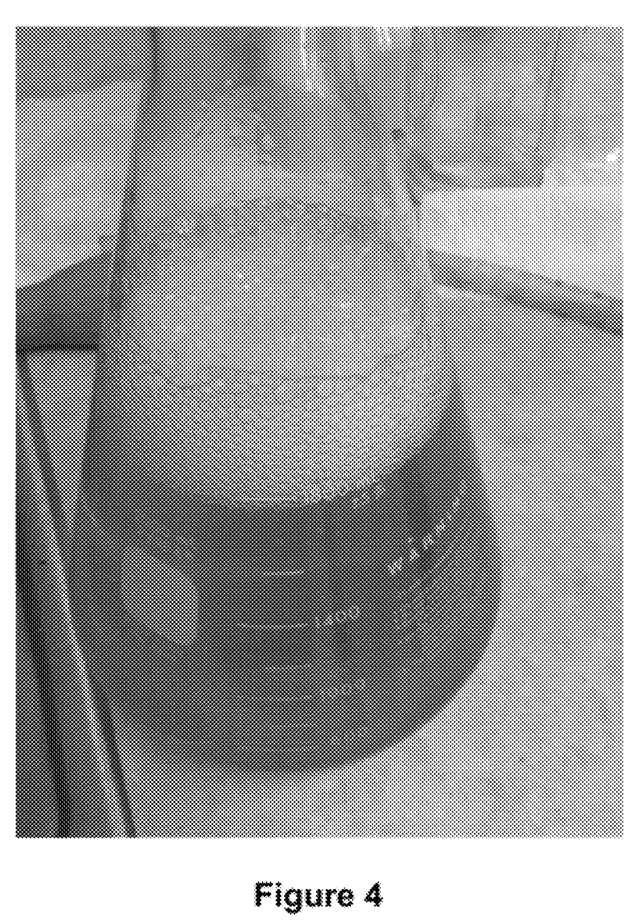
FIG. 4 is a photo showing the vacuum degassing process of a super-saturated oil-gas product obtained through high shear processing.

In some embodiments, the super-saturated solution is stable at ambient conditions for extended periods of time. In some embodiments, the release of the gas from the solution requires the application of vacuum, for example, see FIG. 4.

In an embodiment, the solution is supersaturated with the gas. In some embodiments, the solution is no less than 5% supersaturated with the gas. In some embodiments, the solution is no less than 10% supersaturated with the gas. In some embodiments, the solution is no less than 15% supersaturated with the gas. In some embodiments, the solution is no less than 20% supersaturated with the gas. In some embodiments, the solution is no less than 25% supersaturated with the gas. In some embodiments, the solution is no less than 30% supersaturated with the gas. In some embodiments, the solution is no less than 35% supersaturated with the gas. In some embodiments, the solution is no less than 40% supersaturated with the gas. In some embodiments, the solution is no less than 45% supersaturated with the gas. In some embodiments, the solution is no less than 50% supersaturated with the gas.

Gas. In an embodiment, the gas is selected from the group consisting of nitrogen, carbon dioxide, hydrogen, hydrogen sulfide, a noble gas, and combinations thereof.

Oil. In this disclosure, oil comprises a vegetable oil. A vegetable oil comprises soybean oil, sunflower oil, coconut oil, corn oil, cottonseed oil, olive oil, palm oil, peanut oil (ground nut oil), rapeseed oil (including canola oil), safflower oil, sesame oil, hazelnut oil, almond oil, cashew oil, macadamia oil, mongongo nut oil (or manketti oil), pecan oil, pistachio oil, sacha inchi (plukenetia volubilis) oil, walnut oil, watermelon seed oil, bottle gourd oil, buffalo gourd oil, butternut squash seed oil, or pumpkin seed oil.

Other types of vegetable oil include acai oil, blackcurrant seed oil, borage seed oil, evening primrose oil, carob seed pods, amaranth oil, apricot oil, apple seed oil, argan oil, artichoke oil, avocado oil, babassu oil, ben oil, borneo tallow nut oil, cape chestnut oil (Yangu oil), carob pod oil (algaroba oil), cassia oil, cocoa butter, cocklebur oil, and cohune oil. Further examples of vegetable oil are coriander seed oil, dika oil, false flax oil, flax seed oil, grape seed oil, hemp oil, kapok seed oil, kenaf seed oil, lallemantia oil, manila oil, meadowfoam seed oil, mustard oil, nutmeg butter, okra seed oil, papaya seed oil, perilla seed oil, and pequi oil.

Additional types of vegetable oil include pine nut oil, prune kernel oil, quinoa oil, ramtil oil, rice bran oil, royle oil, tea seed oil (camellia oil), thistle oil, tigernut oil (or nut-sedge oil), tomato seed oil, and wheat germ oil.

Vegetable oils that are used for biofuel may also be processed using the method disclosed herein. Some examples are castor oil, coconut oil (copra oil), corn oil, cottonseed oil, false flax oil, hemp oil, mustard oil, palm oil, peanut oil, radish oil, rapeseed oil, ramtil oil, rice bran oil, safflower oil, salicornia oil, soybean oil, sunflower oil, tigernut oil, and tung oil. Some further examples are algae oil, copaiba, honge oil, jatropha oil, jojoba oil, milk bush, and petroleum nut oil.

Some drying oils (vegetable oils that dry to a hard finish at normal room temperature) may also be processed similarly, such as, walnut oil, sunflower oil, safflower oil, dammar oil, linseed oil, poppyseed oil, stillingia oil (also called Chinese vegetable tallow oil), tung oil, and vernonia oil.

The vegetable oil in this disclosure also includes citrus oils, such as lemon oil, orange oil, grapefruit seed oil, amur cork tree fruit oil, balanos oil, bladderpod oil, brucea javanica oil, burdock oil (bur oil), candlenut oil, carrot seed oil, castor oil, chaulmoogra oil, crambe oil, cuphea oil, illipe butter, jojoba oil, mango oil, mowrah butter, neem oil, ojon oil, rose hip seed oil, rubber seed oil, sea buckthorn oil, shea butter, snowball seed oil (viburnum oil), tall oil, tamanu oil, and tonka bean oil (Cumaru oil).

In some cases, the oil in this disclosure includes any triglyceride oil with unsaturation. This includes soy, corn, palm and fish oils. It also includes ostrich oil.

High Shear Device. High shear devices (HSD) such as high shear mixers and high shear mills are generally divided into classes based upon their ability to mix fluids. Mixing is the process of reducing the size of inhomogeneous species or particles within the fluid. One metric for the degree or thoroughness of mixing is the energy density per unit volume that the mixing device generates to disrupt the fluid. The classes are distinguished based on delivered energy density. There are three classes of industrial mixers having sufficient energy density to create dispersions with particle or bubble sizes in the range of about 0.001 µm to about 50 µm consistently.

Homogenization valve systems are typically classified as high-energy devices. Fluid to be processed is pumped or injected under very high pressure through a narrow-gap valve into a lower pressure environment. The pressure gradients across the valve and the resulting turbulence and cavitations act to break-up and mildly shear any particles, long chain molecules, bubbles, micelles, or different phases in the fluid. These valve systems are most commonly used in milk homogenization and may yield average particle size range from about 0.01 µm to about 1 µm. At the other end of the spectrum are fluid mixer systems classified as low energy devices. These systems usually have paddles or fluid rotors that turn at high speed in a reservoir of fluid to be processed, which in many of the more common applications is a food product. These systems are usually used when average particle, globule, or bubble, sizes of greater than 20 microns are acceptable in the processed fluid.

Between low energy, high shear mixers and homogenization valve systems, in terms of the mixing energy density delivered to the fluid, are colloid mills, which are classified as intermediate energy devices. The typical colloid mill configuration includes a conical or disk rotor that is separated from a complementary, liquid-cooled stator by a closely controlled rotor-stator gap, which may be in the range from about 0.25 µm to 10.0 mm. Rotors may be driven, for example, by an electric motor via direct drive, or alternatively, a belt mechanism. Many colloid mills, with proper adjustments, may achieve average particle, or bubble, sizes of about 0.001 µm to about 25 µm in the processed fluid. These capabilities render colloid mills appropriate for a variety of applications including, but not limited to: colloidal and oil/water-based dispersion processing. In certain instances, the colloid mills can be applied to processes such as preparation of cosmetics, mayonnaise, silicone/silver amalgam, roofing-tar mixtures, and certain paint products.

Figure 1:
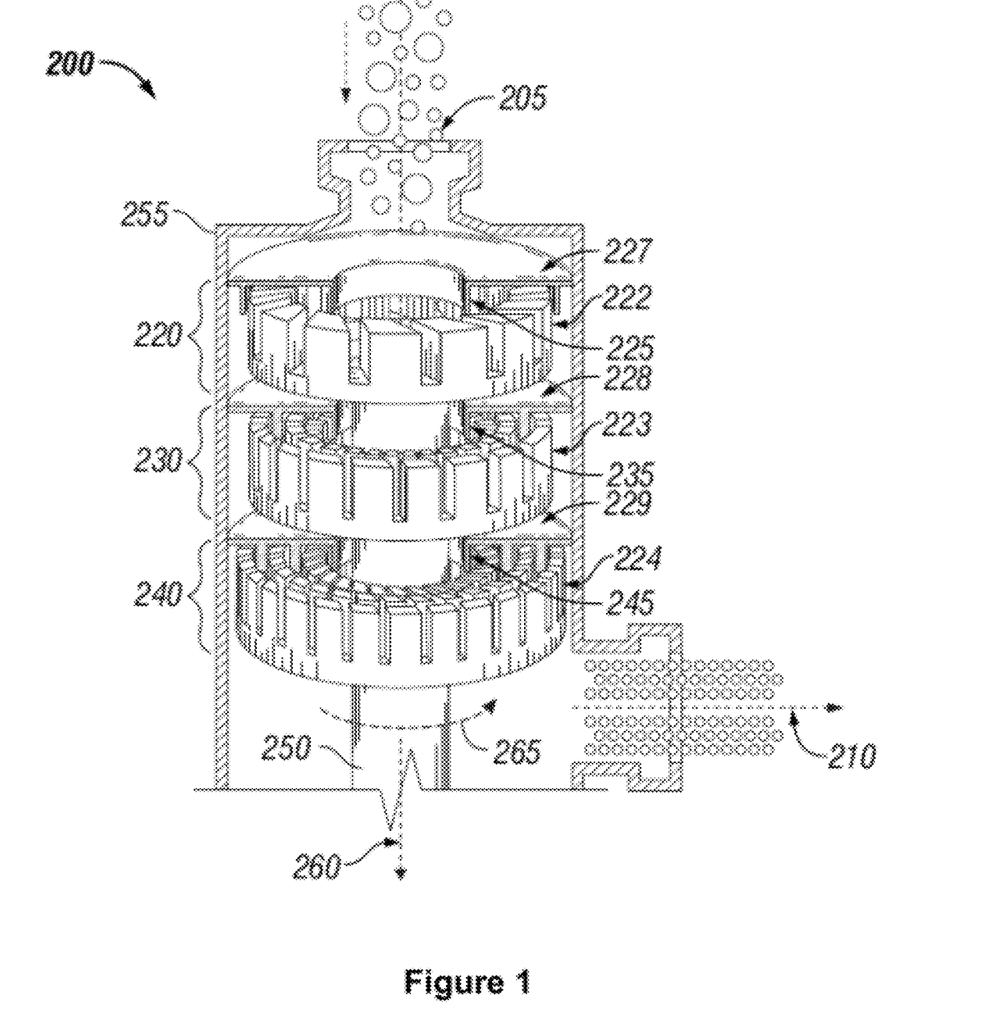
FIG. 1 is a cross-sectional diagram of a high shear device for processing an oil according to an embodiment of this invention.

Referring now to FIG. 1, there is presented a schematic diagram of a high shear device 200. High shear device 200 comprises at least one rotor-stator combination. The rotor-stator combinations may also be known as generators 220, 230, 240 or stages without limitation. The high shear device 200 comprises at least two generators, and most preferably, the high shear device comprises at least three generators. The first generator 220 comprises rotor 222 and stator 227. The second generator 230 comprises rotor 223, and stator 228; the third generator comprises rotor 224 and stator 229. For each generator 220, 230, 240 the rotor is rotatably driven by input 250. The generators 220, 230, 240 are configured to rotate about axis 260, in rotational direction 265. Stator 227 is fixably coupled to the high shear device wall 255.

The generators include gaps between the rotor and the stator. The first generator 220 comprises a first gap 225; the second generator 230 comprises a second gap 235; and the third generator 240 comprises a third gap 245. The gaps 225, 235, 245 are between about 0.25 µm ($10^{-5}$ in) and 10.0 mm (0.4 in) wide. Alternatively, the process comprises utilization of a high shear device 200 wherein the gaps 225, 235, 245 are between about 0.5 mm (0.02 in) and about 2.5 mm (0.1 in). In certain instances, the gap is maintained at about 1.5 mm (0.06 in). Alternatively, the gaps 225, 235, 245 are different between generators 220, 230, 240. In certain instances, the gap 225 for the first generator 220 is greater than about the gap 235 for the second generator 230, which is greater than about the gap 245 for the third generator 240.

Additionally, the width of the gaps 225, 235, 245 may comprise a coarse, medium, fine, and super-fine characterization correlating to a decrease in the size of the gaps 225, 235, 245. Rotors 222, 223, and 224 and stators 227, 228, and 229 may be toothed designs. Each generator may comprise two or more sets of rotor-stator teeth, as known in the art. Rotors 222, 223, and 224 may comprise a number of rotor teeth circumferentially spaced about the circumference of each rotor. Stators 227, 228, and 229 may comprise a number of stator teeth circumferentially spaced about the circumference of each stator.

In certain embodiments, the rotor teeth have uniform spacing about the circumference of each rotor 222, 223, and 224. For example, the distance between each tooth may be between about 0.5 mm (0.02 in) and about 2.5 mm (0.1 in), alternatively, between about 0.5 mm (0.02 in) and about 1.5 mm (0.06 in). In certain instances, the gap is maintained at about 1.5 mm (0.06 in). In instances, the distance between each tooth on each rotor 222, 223, and 224 may be different. Without limitation by theory, altering the gap in the teeth of the rotor may 222, 223, and 224 pulse the shear rate with each revolution of the rotor.

In certain embodiments, the stator teeth have uniform spacing about the circumference of each stator 227, 228, and 229. For example, the distance between each tooth may be between about 0.5 mm (0.02 in) and about 2.5 mm (0.1 in), alternatively, between about 0.5 mm (0.02 in) and about 1.5 mm (0.06 in). In certain instances, the gap is maintained at about 1.5 mm (0.06 in). In instances, the distance between each tooth on each stator 227, 228, and 229 may be different. Without limitation by theory, altering the gap in the teeth may configure the stator 227, 228, and 229 to pulse the shear rate with each revolution of the rotor.

In embodiments, the inner diameter of the rotor is about 11.8 cm. In embodiments, the outer diameter of the stator is about 15.4 cm. In further embodiments, the rotor and stator may have an outer diameter of about 60 mm for the rotor, and about 64 mm for the stator. Alternatively, the rotor and stator may be configured with alternate diameters in order to increase the tip speed and shear pressures, for instance in a commercial scale device. Without limitation by theory, a commercial scale rotor and stator may have considerably larger diameters, measure in meters, for instances. In certain embodiments, each of three stages is operated with a superfine generator, comprising a gap of between about 0.025 mm and about 3 mm. When a feed stream 205, comprising a dispersible phase and a continuous phase, is sent through high shear device 200, a gap width is predetermined to achieve a desired dispersion.

Feed stream 205 comprises a continuous phase and a dispersible phase for forming dispersion after high shear mixing. In certain instances, the continuous phase of feed stream 205 comprises a liquid stream, for instance oil. The continuous phase may further comprise a solvent, a carrier liquid, or a reactant carrier, without limitation. The dispersible phase of feed stream 205 comprises a gas or vapor, such as steam, for dispersion into the continuous phase. Alternatively, the dispersible phase comprises a gas dissolved in a carrier liquid, which will not readily mix and/or dissolve in the continuous phase. In instances where the feed stream 205 is to be reacted with gases, the dispersible phase comprises: gas bubbles, gas particles, vapor droplets, globules, micelles, or combinations thereof. The feed stream 205 may include a particulate solid component, for instance a catalyst, in the dispersible phase. As used herein, the dispersible phase including gases, liquids and solids, comprises particles. In certain instances, feed stream 205 comprises a heterogeneous mixture of the dispersible phase in the continuous phase. The heterogeneous mixture may be highly viscous liquid, such as slurries or pastes. As used herein, heterogeneous mixture encompasses a continuous phase comprising an oil stream in the dispersible phase. Without being limited by any particular theory, the feed stream 205 comprising a heterogeneous mixture has a continuous phase and a dispersible phase prior to or simultaneous with introduction to high shear device 200.

Feed stream 205 introduced to high device 200 is pumped through the generators 220, 230, 240, such that product dispersion 210 is formed. Product dispersion 210 comprises particles of the dispersible phase homogeneously distributed through the continuous phase. In each generator, the rotors 222, 223, 224 rotate at high speed relative to the fixed stators 227, 228, 229. The rotation of the rotors forces fluid, such as the feed stream 205, between the outer surface of the rotor 222 and the inner surface of the stator 227 creating localized high shear conditions. The gaps 225, 235, 245 generate high shear forces that process the feed stream 205. The high shear forces between the rotor and stator form a more homogeneous dispersion of the dispersible phase particles in the continuous phase, to form the product dispersion 210. Additionally, the high shear forces reduce the mean particle size. Each generator 220, 230, 240 of the high shear device 200 has interchangeable rotor-stator combinations for producing a narrow distribution of the desired particle size. Without limitation by theory, the rotor-stator combinations are selected to form a desired dispersion and particle size.

The product dispersion 210 has an average particle size less than about 1.5 µm; in certain instances the particles are submicron in diameter. In certain instances, the average particle size is in the range from about 1.0 µm to about 0.1 µm. Alternatively, the average particle size is less than about 400 nm (0.4 µm) and most preferably less than about 100 nm (0.1 µm). Preferably, the globules are at least micron sized. In instances, the high shear device 200 is configured to produce micron-size steam dispersions in oil. In embodiments, the generators 220, 230, 240 are configured to produce steam dispersions with average particle or globule size ranging from about 1 micron to about 500 microns in diameter. In certain embodiments, the globule size is about 50 microns in diameter. The globule sizes are be controllable by the amount of shear applied to the fluid and the configuration of the generators 220, 230, 240 as described previously.

Tip speed is the velocity (m/sec) associated with the end of one or more revolving elements that is transmitting energy to the contents in the high shear device. Tip speed, for a rotating element, is the circumferential distance traveled by the tip of the rotor per unit of time, and is generally defined by the equation V (m/sec)=π·D·n, where V is the tip speed, D is the diameter of the rotor, in meters, and n is the rotational speed of the rotor, in revolutions per second. Tip speed is thus a function of the rotor diameter and the rotation rate. In certain embodiments, altering the diameter or the rotational rate may increase the shear rate in high shear device 200.

For colloid mills, typical tip speeds are in excess of 23 m/sec (4500 ft/min) and may exceed 40 m/sec (7900 ft/min). For the purpose of the present disclosure the term 'high shear' refers to mechanical rotor-stator devices, such as mills or mixers, that are capable of tip speeds in excess of 1 m/sec (200 ft/min) and require an external mechanically driven power device to drive energy into contents in the high shear device. A high shear device combines high tip speeds with a very small shear gap to produce significant friction on the material being processed. Accordingly, a local pressure in the range of about 1000 MPa (about 145,000 psi) to about 1050 MPa (152,300 psi) and elevated temperatures at the tip are produced during operation. In certain embodiments, the local pressure is at least about 1034 MPa (about 150,000 psi). The local pressure further depends on the tip speed, fluid viscosity, and the rotor-stator gap during operation.

The shear rate is the tip speed divided by the shear gap width (minimal clearance between the rotor and stator). An approximation of energy input into the fluid (kW/l/min) may be made by measuring the motor energy (kW) and fluid output (l/min). In embodiments, the energy expenditure of a high shear device is greater than 1000 W/m$^3$. In embodiments, the energy expenditure is in the range of from about 3000 W/m$^3$ to about 7500 W/m$^3$.

The high shear device 200 combines high tip speeds with a very small shear gap to produce significant shear on the material. The amount of shear is typically dependent on the viscosity of the fluid and the shear gap. The shear rate generated in a high shear device 200 may be greater than 20,000 s$^{-1}$. In embodiments, the shear rate generated is in the range of from 20,000 s$^{-1}$ to 100,000 s$^{-1}$. The shear rate generated in HSD 40 may be in the greater than 100,000 s$^{-1}$. In some embodiments, the shear rate is at least 500,000 s$^{-1}$. In some embodiments, the shear rate is at least 1,000,000 s$^{-1}$. In some embodiments, the shear rate is at least 1,600,000 s$^{-1}$. In embodiments, the shear rate generated by HSD 40 is in the range of from 20, s$^{-1}$ to 100,000 s$^{-1}$. For example, in one application the rotor tip speed is about 40 m/s (7900 ft/min) and the shear gap width is 0.0254 mm (0.001 inch), producing a shear rate of 1,600,000 s$^{-1}$. In another application, the rotor tip speed is about 22.9 m/s (4500 ft/min) and the shear gap width is 0.0254 mm (0.001 inch), producing a shear rate of about 901,600 s$^{-1}$.

The rotor is set to rotate at a speed commensurate with the diameter of the rotor and the desired tip speed as described hereinabove. Without being limited by theory, transport resistance is reduced by incorporation of high shear device 200 such that the dispersion of steam in oil is increased. Alternatively, the high shear device 200 comprises a high shear colloid mill that serves to accelerate reactions downstream and in the reactor due to the formation of free radicals created by the high pressures and temperatures present instantaneously at the tip of the rotating high shear device. Accelerating reactions downstream from the high shear device 200 may utilize a single stage or dispersing chamber, in certain instances. Further, in alternate configurations accelerating reactions downstream may include a plurality of inline devices, for instance comprising at least 2 stages.

Selection of the high shear device 200 is dependent on throughput requirements and desired particle size in the outlet dispersion 210. In certain instances, high shear device 200 comprises a Dispax Reactor® of IKA® Works, Inc. Wilmington, NC and APV North America, Inc. Wilmington, MA. Model DR 2000/4, for example, comprises a belt drive, 4M generator, PTFE sealing ring, inlet flange 1" sanitary clamp, outlet flange ¾" sanitary clamp, 2HP power, output speed of 7900 rpm, flow capacity approximately 300 l/h to approximately 700 l/h (depending on generator), a tip speed of from 9.4 m/s to above about 41 m/s (about 1850 ft/min to above about 8070 ft/min). Several alternative models are available having various inlet/outlet connections, horsepower, tip speeds, output rpm, and flow rate. In further instances, the high shear device 200 comprises any device with configured to produce the high shear rate and throughput for forming a product dispersion.

Without wishing to be limited to any particular theory, it is believed that the degree of high shear mixing in a high shear device is sufficient to increase rates of mass transfer. Further, a high shear device may produce localized non-ideal conditions that enable formation of free radicals and reactions to occur that would not otherwise be expected to occur based on Gibbs free energy predictions. Additionally, such reactions would not be expected at low shear mixing parameters. Localized non-ideal conditions are believed to occur within the high shear device resulting in increased temperatures and pressures with the most significant increase believed to be in localized pressures. The increase in pressures and temperatures within the high shear device are instantaneous and localized. In certain instances, the temperature and pressure increases revert to bulk or average system conditions once exiting the high shear device. In some cases, the high shear-mixing device induces cavitation of sufficient intensity to dissociate one or more of the reactants into free radicals, which may intensify a chemical reaction or allow a reaction to take place at less stringent conditions than might otherwise be required. Cavitation may also increase rates of transport processes by producing local turbulence and liquid microcirculation (acoustic streaming). An overview of the application of cavitation phenomenon in chemical/physical processing applications is provided by Gogate et al., "Cavitation: A technology on the horizon," Current Science 91 (No. 1): 35-46 (2006). For high shear processing of an oil and a gas, the high shear action is able to incorporate gas molecules into an oil molecule forming an internal inert blanket, thus generating stabilization effects for the produced dispersion.

Figure 2A:
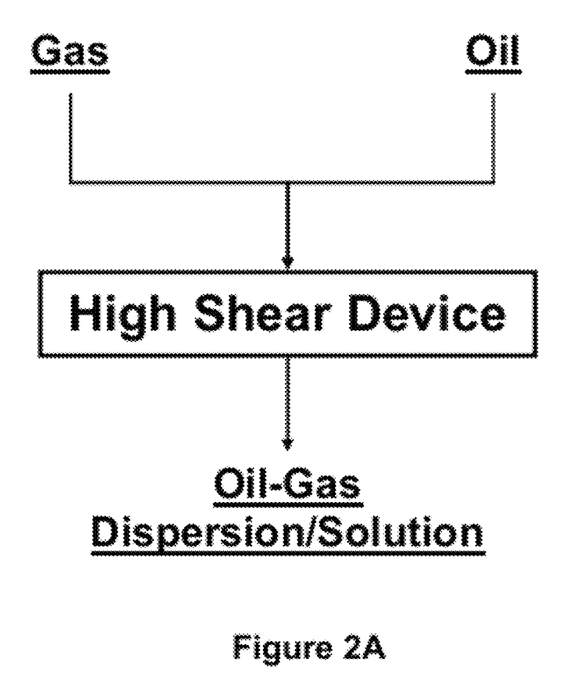
FIG. 2A illustrates a method of processing an oil according to an embodiment of this invention.
Figure 5A:
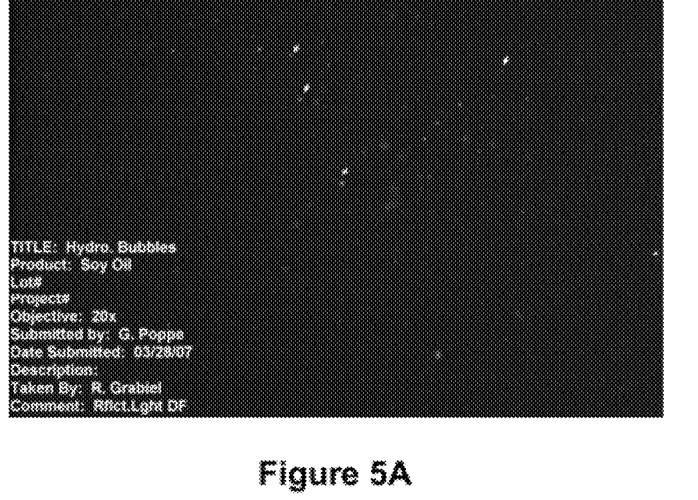
FIGS. 5A-5C are scanning electron micrographs showing hydrogen bubbles in oil after high shear processing. The hydrogen bubbles as shown have a diameter of from about 0.5 micron to about 2 micron.
Figure 5B:
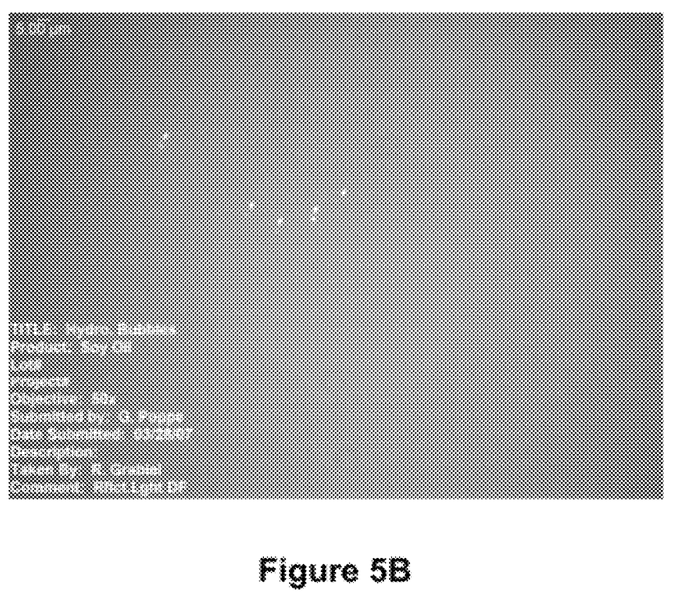
Figure 5C:
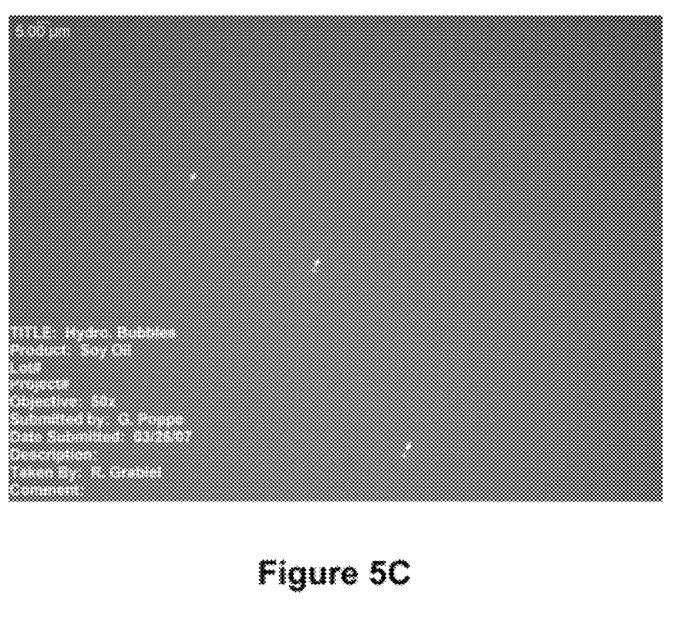

High Shear Processing of Oil. In an embodiment as illustrated by FIG. 2A, an oil and a gas are mixed in a high shear device (HSD) to form oil-gas dispersion/solution. In some embodiments, the oil-gas dispersion/solution contains gas bubbles with a diameter of less than about 50 μm, as shown in FIGS. 5A-5C. In some embodiments, the oil-gas dispersion/solution contains gas bubbles with a diameter of less than about 20 μm, as shown in FIGS. 5A-5C. In some embodiments, the oil-gas dispersion/solution contains gas bubbles with a diameter of less than about 10 μm, as shown in FIGS. 5A-5C. In some embodiments, the oil-gas dispersion/solution contains gas bubbles with a diameter of less than about 5 μm, as shown in FIGS. 5A-5C. In some embodiments, the oil-gas dispersion/solution contains gas bubbles with a diameter of less than about 2 μm, as shown in FIGS. 5A-5C. In various embodiments, the oil-gas dispersion/solution comprises nanobubbles of the gas. As used herein, "nanobubbles" refers to gas bubbles with a size in the range of from sub-nanometers to 1000 nanometers in diameter. In some embodiments, the shear device produces a dispersion/solution having a mean bubble size of less than about 5 μm in diameter. In some embodiments, the bubbles in the produced dispersion/solution are sub-micron in diameter. In some embodiments, the average bubble size is from about 0.1 μm to about 5 μm in diameter. In some embodiments, the shear device produces a dispersion/solution having a mean bubble size of less than 400 nm in diameter. In some embodiments, the shear device produces a dispersion/solution having a mean bubble size of less than 100 nm in diameter.

Figure 2B:
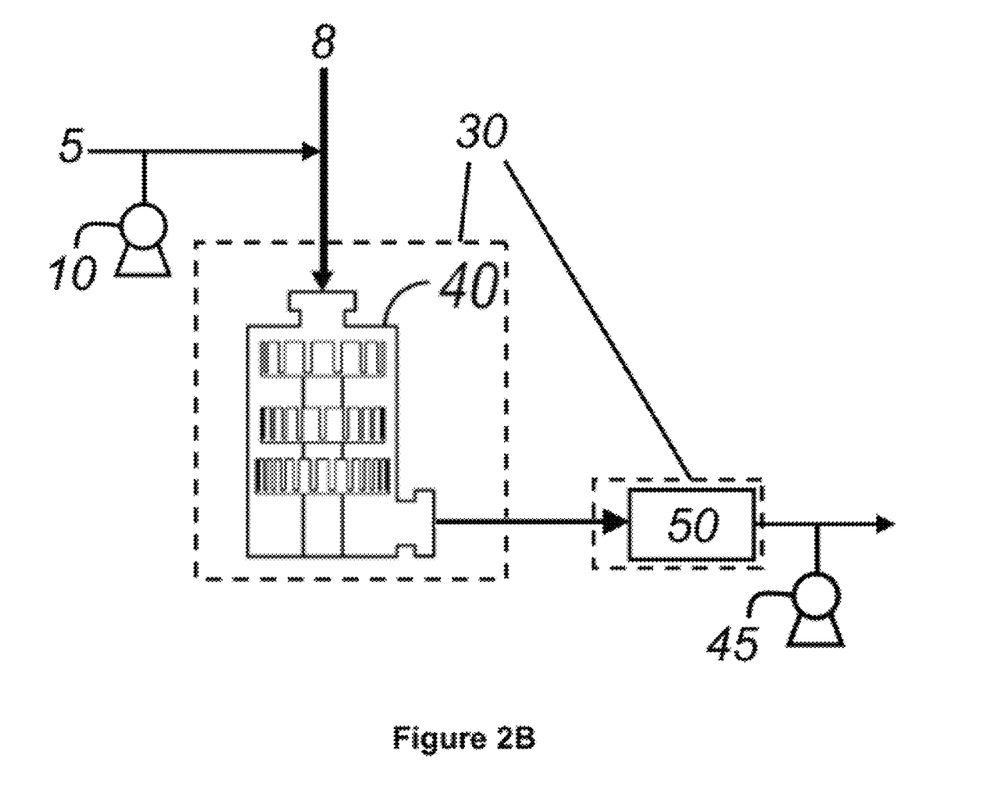
FIG. 2B illustrates a schematic diagram of a high shear oil processing system according to an embodiment of this invention.

Referring to FIG. 2B, an oil 5 and a gas 8 are introduced into shear device 40 (at inlet 205 in FIG. 1). The gas is dispersed into nanobubbles in the oil. In some embodiments, a pump 10 is included to control the flow rate of the oil into shear device 40. Pump 10 is configured for either continuous or semi-continuous operation, and may be any suitable pumping device. In some embodiments, a pump is used to control the flow rate of the gas into shear device 40 (not shown in FIG. 2B). In some cases, oil 5 and gas 8 are mixed together before being introduced to HSD 40. In some other cases, oil 5 and gas 8 are directly introduced to HSD 40 (not shown in FIG. 2B).

In some embodiments, a storage vessel 50 is included in the high shear system (HSS) shown in FIG. 2B to receive the produced dispersion/solution from HSD 40. Pump 45 is utilized to extract the dispersion/solution from vessel 50 and configured to control the flow rate of the dispersion/solution. Pump 45 or pump 10 is configured for either continuous or semi-continuous operation, and may be any suitable pumping device that is capable of providing greater than about 202.65 kPa (2 atm) pressure, preferably greater than about 303.975 kPa (3 atm) pressure, to allow controlled flow through HSD 40 and throughout the HSS. Preferably, all contact parts of the pump(s) comprise stainless steel, for example, 316 stainless steel. In addition to pump 10 and pump 45, one or more additional pumps (not shown) may be included in the HSS illustrated in FIG. 2B. For example, a booster pump, which may be similar to pump 45, may be included between HSD 40 and vessel 50 for boosting the pressure. As another example, a supplemental feed pump, which may be similar to pump 10, may be included for introducing additional gas or oil to HSD 40. A Roper Type 1 gear pump, Roper Pump Company (Commerce Ga.) Dayton Pressure Booster Pump Model 2P372E, Dayton Electric Co (Niles, Ill.) is an example for the HSS shown in FIG. 2B.

In various embodiments, a temperature control system 30 may be included in the HSS. The temperature control system is configured to control the temperature of the HSD 40 and/or the storage vessel 50 to ensure that the mixing of the gas and the oil takes place at a temperature that the oil is in its liquid phase and that the gas has sufficient solubility to be incorporated into the oil to cause stabilizing effects. In certain instances, temperature control system comprises heat exchangers. Oil feed stream 5 may be heated or cooled using any method known to one skilled in the art. The use of external heating and/or cooling heat transfer devices for changing the temperature of oil feed stream 5 is also contemplated. Some examples of such heat exchangers are shell, tube, plate, and coil heat exchangers, as are known in the art.

In embodiments, HSD 40 comprises a plurality of high shear generators to form a dispersion/solution. HSD 40 comprises at least a high shear, three stage dispersing device configured with three rotors in combination with stators, aligned in series. For example, disperser IKA® model DR 2000/4, may be used as HSD 40, to create the dispersion/solution of gas in the oil. The rotor-stator sets may be configured as illustrated for example in FIG. 1. The rotors of HSD 40 may be set to rotate at a speed commensurate with the diameter of the rotor and the desired tip speed. As described above, the high shear device (e.g., colloid mill or toothed rotor) has either a fixed clearance between the stator and rotor or has adjustable clearance. The mixing and shear in HSD 40 is increased at a rotor-stator by decreasing the rotor-stator gaps, or increasing the rotational rate of the rotor, and vice-versa. HSD 40 delivers at least 300 L/h at a tip speed of at least 4500 ft/min, and which may exceed 7900 ft/min (40 m/s). The high shear mixing results in dispersion/solution of micron or submicron-sized gas bubbles in a continuous liquid phase comprising oil. Further, the HSD 40 may comprise any components and operating conditions configurable and operable to achieve a desired shear between the rotor-stators.

In HSD 40, the rotors and stators of the stages may have circumferentially spaced first stage rotor teeth and stator teeth, respectively. In certain configurations, the rotor-stator gap decreases stepwise from stage to stage. Alternatively, the rotor-stator gap is configured to be constant from stage to stage. Further, HSD 40 may comprise a heat exchanger. In non-limiting examples, a heat exchanger for HSD 40 comprises a conduit for directing a thermal fluid in contact with a thermally conductive portion of the device. More specifically, HSD 40 comprises a PTFE seal that may be cooled using any suitable technique that is known in the art.

HSD 40 is configured to flow the HSD feed stream through the rotor-stator stages to form a dispersion/solution. In instances, HSD feed stream enters a first stage rotor-stator combination and is subjected to the mixing and shear of the first stage. The coarse dispersion/solution exiting the first stage enters the second rotor-stator stage, and is subjected to increased mixing and shear. The further reduced, or intermediate, bubble-size dispersion/solution emerging from the second stage enters the third stage rotor-stator combination. The third stage rotor-stator is configured to produce the comparatively highest mixing and shear conditions. Configured thus, HSD 40 sequentially increases the mixing and shear conditions at each stage. Alternatively, the shear rate is substantially constant along the direction of the flow, with the shear rate in each stage being substantially the same. In another configuration, the shear rate in the first rotor-stator stage is greater than the shear rate in subsequent stage(s).

The HSD feed stream is subjected to the high shear conditions in the HSD. The gas stream 8 and oil stream 5 of HSD feed stream are mixed within HSD 40, which serves to create a fine dispersion/solution of the gas in the oil. HSD 40 serves to intimately mix the gas and oil under high shear conditions. In HSD 40, the gas and oil are highly dispersed such that nanobubbles, submicron-sized bubbles, and/or microbubbles of gas are formed in the oil. The resultant dispersion/solution has an average bubble size less than about 1.5 µm. Accordingly, the dispersion/solution exiting HSD 40 comprises micron and/or submicron-sized gas bubbles. In some embodiments, the resultant dispersion/solution has an average bubble size less than 1 µm. In some embodiments, the mean bubble size is in the range of about 0.4 µm to about 1.5 µm. In some embodiments, the mean bubble size is less than about 400 nm, and may be about 100 nm in some cases. Bubble size is dependent on local pressures and temperatures and may be estimated by ideal gas laws. In embodiments, the dispersion/solution is able to remain dispersed at atmospheric pressure for at least about 15 minutes.

Figure 3:
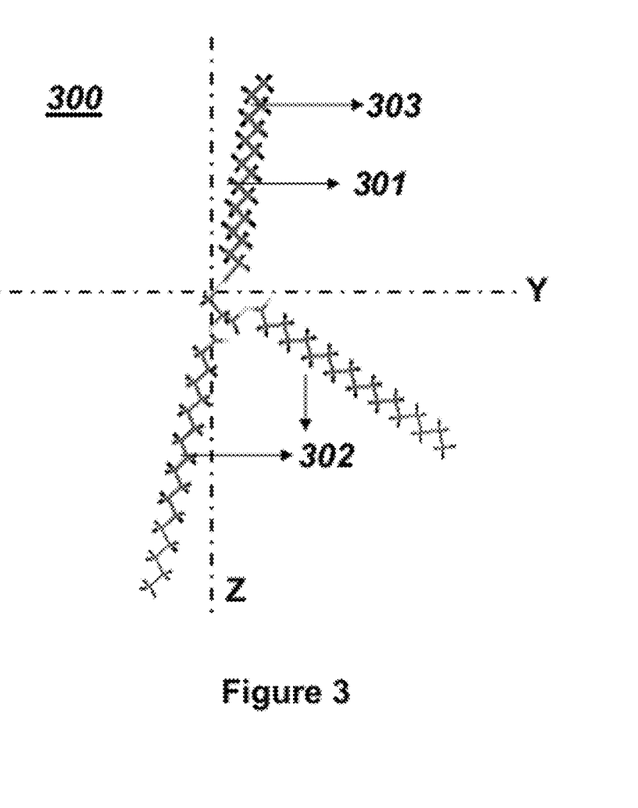
FIG. 3 illustrates an oil molecule with vacant ports to embed gas molecules according to an embodiment of this invention.

Without wishing to be limited by a theory, the gas may be incorporated or embedded into an oil molecule and thus super-saturate the oil. In other words, the solubility of gas in oil is increased by the high shear action. An example of an oil molecule is shown in FIG. 3. In FIG. 3, molecule 300 is tristearin for 1,3-di(octadecanoyloxy)propan-2-yl octadecanoate or tristearin or trioctadecanoin or glycerol tristearate or glyceryl tristearate), which is a triglyceride, a glyceryl ester of stearic acid, derived from fats. Molecule 300 has backbone 301, branches 302, and vacant ports 303. Furthermore, molecule 300 is able to freely spin around axis Y or axis Z. Gas molecules are latched onto such an oil molecule (300) via the vacant ports 303, especially under the action of high shear. Such an incorporation formed between the oil molecule and the gas molecule promotes the stabilization effects, resulting in prevention and/or retardation of oxidation of the oil.

In some embodiments, oil is degassed under vacuum to remove a proportion of the air dissolved in the oil prior to passing through the high shear device. In some embodiments, the oil is heated or cooled prior to passing through the high shear device. In some cases, the oil is heated or cooled to a temperature, for example, just above the solidification temperature of the particular oil. In some cases the oil is heated to aid in flow or to solubilize the oil.

The temperature of mixing the gas with the oil depends on the melting point of the oil and the relationship between the gas solubility and temperature. Since most vegetable oils are liquids at ambient temperature and gases tend to have high solubilities with decreasing temperatures, in many cases the high shear process takes place at a temperature no greater than room/ambient temperature. As discussed earlier, vegetable fats may be processed in the same way. The operating temperature may change depending on the properties of the vegetable fat that is to be processed. Generally speaking, the vegetable oil/fat is processed at a temperature that the oil/fat is in its liquid phase and gives the gas sufficient solubility for high shear mixing.

In an embodiment, the high shear mixing of oil and gas takes place in the presence of a catalyst. In some cases, the catalyst is a copper chromite catalyst. In some cases, the catalyst is activated charcoal. The use of a catalyst depends on the desired processes or reactions. In some embodiments, an oil is alkylated, oxidized, hydrogenated or dehydrogenated. Each of such reactions is catalyzed by a suitable catalyst, which catalyst is known to one skilled in the art. The processing temperature is no greater than the boiling point of the oil at the pressure at which the process takes place. In an embodiment, a catalyst is not required to provide saturation or super saturation of the oil.

Multiple High Shear Mixing Devices. In certain instances, two or more high shear devices are used to further enhance the stabilization effects of the gas on the oil. Their operation may be in either batch or continuous mode. In instances, a high shear processing system comprises configuration and process flow changes to derive benefit for the implementation of multiple high shear device arrangements.

Integrated Method and System. In some embodiments, the high shear processing method and system are integrated with an existing oil production method and system.

The mixing of a gas with the oil under high shear may be applied anywhere in an existing oil refining or post refining process. In some cases, it is after the oil is refined (commonly referred to as R oil). In some cases, it is after the oil is bleached (commonly referred to as RB oil). In some cases, it is after the oil is deodorized (commonly referred to as RBD oil). In some other cases, it is after the oil is hydrogenated. In some other cases, hydrogen is combined with the gas to provide hydrogenation and internal inert blanketing. In some cases, a high shear device is used in combination with steam stripping to promote steam dispersion throughout the oil and enhance stripping as well as removal of absorbed oxygen, which further stabilizes unsaturated oils.

The processing of soy oil is typical of that used with most vegetable oils. Crude oil, straight from the crushing operation, is first mixed with caustic soda. Saponification turns triglycerides into soap. The soap is removed with a centrifuge. Neutralized dry soap stock (NDSS) is typically used in animal feed. The remaining oil is deodorized by heating under a near-perfect vacuum and sparged with water. More specifically, the oil is heated under vacuum to near the smoke point, and water is introduced at the bottom of the oil. The water immediately is converted to steam, which bubbles through the oil, carrying with it any chemicals which are water-soluble. The steam sparging removes impurities that impart unwanted flavors and odors to the oil. The condensate is further processed to become vitamin E food supplement, while the oil may be sold to manufacturers and consumers.

In some cases, some of the oil is further processed. By carefully filtering the oil at near-freezing temperatures, "winter oil" is produced. This oil may be made into salad dressings. In some other cases, the oil is partially hydrogenated to produce various ingredient oils. Lightly hydrogenated oils have very similar physical characteristics to regular soy oil, but are more resistant to becoming rancid or oxidized. The lightly hydrogenated oils may go through the high shear process as described herein to strengthen its resistance to rancidification/oxidation. For fry oils produced from vegetable oils, substantial hydrogenation is required to keep the polyunsaturates of oil (e.g., soy oil) from becoming rancid. Hydrogenated vegetable oils differ in two major ways from other oils which are equally saturated. During hydrogenation, it is easier for hydrogen to come into contact with the fatty acids on the end of the triglyceride, and less easy for them to come into contact with the center fatty acid. Trans fatty acids (often called trans fat) are formed in the hydrogenation process, and may amount to as much as 40 percent by weight of a partially hydrogenated oil. Trans fatty acids (or trans fat) are increasingly thought to be unhealthy. The high shear process as described herein is especially useful in producing oils that require high stability or high resistance to rancidification/oxidation. In some cases, oils that pass through the high shear process as described herein do not need to be hydrogenated to the same degree, thereby reducing the content of trans fat in the oil.

In some embodiments, the oil production system comprises degumming unit, a neutralization unit, a bleaching unit, and a deodorization unit. Furthermore, the high shear process may be combined with any known process for removing oil soluble impurities. Conventional method comprises the steps of refining, bleaching, and deodorizing. Caustic refining process comprises degumming, refining, bleaching, and deodorizing a vegetable oil. Physical refining process comprises degumming, bleaching, and deodorizing (steam refining) a vegetable oil. The high shear processing method or system may be combined with one or more of the processes or units utilized for vegetable oil production. The high shear process may be applied anywhere in the production process of the vegetable oil after extraction. In some cases, it is after the oil is deodorized. In some other cases, it is after the oil is hydrogenated. The method and system (system components) for oil production are known in the art.

In an embodiment, high shear processing of oil and gas takes place more than once in an existing oil refining or post refining process. For example, high shear processing takes place between refining and bleaching and also takes place after deodorization of oil. Given the above disclosure, many configurations to integrate the high shear process/system with an existing oil production process/system are conceivable by one skilled in the art. As such, all such configurations are within the scope of this disclosure.

Advantages. In various embodiments, the high shear process increases oil stability, retards or prevents oxidation, preserves valuable compounds contained in the oil, e.g., omega-3 fatty acids.

Stability improvement. All fats and oils are prone to oxidation. The rate of oxidation depends on the degree of unsaturation, the presence of antioxidants, and prior storage conditions. Oil Stability Index (OSI) is an American Oil Chemists Society (AOCS) approved method that determines the relative resistance of fat and oil samples to oxidation. It replaces the outdated AOM (Active Oxygen Method), which is based on measuring peroxide values for determining the induction time of fats and oils.

In the OSI analysis, the rate of oxidation is slow until any resistance to oxidation is overcome. This time is known as the oxidation induction period. After the induction period, the rate of oxidation increases dramatically. Peroxide value and free fatty acid analyses give an idea of how good or bad an oil is at a particular time; whereas the OSI analysis has predictive value. OSI can be used to compare various oils to predict their respective shelf lives. The OSI analysis can also be used to evaluate the effectiveness of antioxidants or determine how much longer a frying oil can be used before it goes bad.

The OSI method is applicable in general to all fats and oils. The most common oils analyzed are refined plant oils (i.e. Soybean, Palm, Peanut, Sunflower, Corn, Coconut, and Canola). The OSI times can range from less than two hours to over 100 hours.

RBD soybean oil (a salad oil) is high shear treated with nitrogen and carbon dioxide (only once). The untreated oil has an OSI of 5 hours at 110° C.; whereas the nitrogen treated oil has an OSI of 5.95 hours at 110° C. and the carbon dioxide treated oil has an OSI of 6.85 hours at 110° C. The untreated oil has an AOM of 10-12 hours; whereas the nitrogen treated oil has an AOM of 13.93 hours and the carbon dioxide treated oil has an AOM of 16.11 hours.

While preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations. The use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, and the like.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the preferred embodiments of the present invention. The inclusion or discussion of a reference is not an admission that it is prior art to the present invention, especially any reference that may have a publication date after the priority date of this application. The disclosures of all patents, patent applications, and publications cited herein are hereby incorporated by reference, to the extent they provide background knowledge; or exemplary, procedural or other details supplementary to those set forth herein.

We claim:

1. A method of producing an oil, the method comprising:
providing a high shear device comprising at least one rotor and at least one complementarily-shaped stator configured to mix a gas with a liquid;
contacting a gas with an organic oil in said high shear device at a temperature above the solidification temperature of the oil such that said oil maintains a liquid phase, wherein said gas is selected from the group consisting of nitrogen, noble gases, and carbon dioxide, thus forming a product, wherein said product is a dispersion comprising a continuous oil phase having gas bubbles dispersed therein, wherein the gas bubbles have a mean diameter of less than 50 μm, and wherein the dispersion is no less than 5% saturated or supersaturated with the gas.

2. The method of claim 1 wherein said gas comprises nitrogen, carbon dioxide, or a combination thereof.

3. The method of claim 1 wherein said oil comprises vegetable oil.

4. The method of claim 1 wherein said oil comprises edible oil or inedible oil.

5. The method of claim 1 wherein said oil comprises soybean oil.

6. The method of claim 1 wherein said oil comprises ostrich oil.

7. The method of claim 1 wherein said oil is selected from the group consisting of soybean oil, sunflower oil, coconut oil, corn oil, cottonseed oil, olive oil, palm oil, peanut oil (ground nut oil), rapeseed oil (including canola oil), safflower oil, sesame oil, hazelnut oil, almond oil, cashew oil, macadamia oil, mongongo nut oil (or manketti oil), pecan oil, pistachio oil, sacha inchi (plukenetia volubilis) oil, walnut oil, watermelon seed oil, bottle gourd oil, buffalo gourd oil, butternut squash seed oil, pumpkin seed oil, acai oil, blackcurrant seed oil, borage seed oil, evening primrose oil, carob seed pods, amaranth oil, apricot oil, apple seed oil, argan oil, artichoke oil, avocado oil, babassu oil, ben oil, borneo tallow nut oil, cape chestnut oil (Yangu oil), carob pod oil (algaroba oil), cassia oil, cocoa butter, cocklebur oil, cohune oil, coriander seed oil, dika oil, false flax oil, flax seed oil, grape seed oil, hemp oil, kapok seed oil, kenaf seed oil, lallemantia oil, manila oil, meadowfoam seed oil, mustard oil, nutmeg butter, okra seed oil, papaya seed oil, perilla seed oil, pequi oil, pine nut oil, prune kernel oil, quinoa oil, ramtil oil, rice bran oil, royle oil, tea seed oil (camellia oil), thistle oil, tigernut oil (or nut-sedge oil), tomato seed oil, wheat germ oil, castor oil, coconut oil (copra oil), corn oil, cottonseed oil, false flax oil, hemp oil, mustard oil, palm oil, peanut oil, radish oil, rapeseed oil, ramtil oil, rice bran oil, safflower oil, salicornia oil, tigernut oil, tung oil, algae oil, copaiba, honge oil, jatropha oil, jojoba oil, milk bush, petroleum nut oil, walnut oil, dammar oil, linseed oil, poppyseed oil, stillingia oil (Chinese vegetable tallow oil), vernonia oil, lemon oil, orange oil, grapefruit seed oil, amur cork tree fruit oil, balanos oil, bladderpod oil, brucea javanica oil, burdock oil (bur oil), candlenut oil, carrot seed oil, castor oil, chaulmoogra oil, crambe oil, cuphea oil, illipe butter, jojoba oil, mango oil, mowrah butter, neem oil, ojon oil, rose hip seed oil, rubber seed oil, sea buckthorn oil, shea butter, snowball seed oil (viburnum oil), tall oil, tamanu oil, tonka bean oil (Cumaru oil), and combinations thereof.

8. A method of producing oil comprising utilizing the method of claim 1 and an existing oil processing method.

9. A method of producing an oil, the method comprising:
providing a high shear device comprising at least one rotor and at least one complementarily-shaped stator configured to mix a gas with a liquid;
contacting a as with an organic oil in said high shear device at a temperature above the solidification temperature of the oil, such that said oil maintains a liquid phase, wherein said gas is selected from the group consisting of nitrogen, noble gases, and carbon dioxide, thus forming a product, wherein said product is a dispersion comprising a continuous oil phase having gas bubbles dispersed therein, wherein the gas bubbles have a mean diameter of less than 50 μm, and wherein the method is applied between refining and bleaching the oil.

10. A method of producing an oil, the method comprising:
providing a high shear device comprising at least one rotor and at least one complementarily-shaped stator configured to mix a gas with a liquid;
contacting a gas with an organic oil in said high shear device at a temperature above the solidification temperature of the oil, such that said oil maintains a liquid phase, wherein said gas is selected from the group consisting of nitrogen, noble gases, and carbon dioxide, thus forming a product, wherein said product is a dispersion comprising a continuous oil phase having gas bubbles dispersed therein, wherein the gas bubbles have a mean diameter of less than 50 μm, and wherein the method is applied after deodorizing the oil.

11. A method of producing an oil, the method comprising:
providing a high shear device comprising at least one rotor and at least one complementarily-shaped stator configured to mix a gas with a liquid;
contacting a gas with an organic oil in said high shear device at a temperature above the solidification temperature of the oil, such that said oil maintains a liquid phase, wherein said gas is selected from the group consisting of nitrogen, noble gases, and carbon dioxide, thus forming a product, wherein said product is a dispersion comprising a continuous oil phase having gas bubbles dispersed therein, wherein the as bubbles have a mean diameter of less than 50 μm, and wherein the method is applied more than once.

12. A method of producing an oil, the method comprising:
providing a high shear device comprising at least one rotor and at least one complementarily-shaped stator configured to mix a gas with a liquid;
heating said oil prior to contacting a gas with the oil in said high shear device at a temperature above the solidification temperature of the oil, such that said oil maintains a liquid phase, wherein said gas is selected from the group consisting of nitrogen, noble gases, and carbon dioxide, thus forming a product, wherein said product is a dispersion comprising a continuous oil phase having as bubbles dispersed therein, wherein the gas bubbles have a mean diameter of less than 50 μm.

13. A method of producing an oil, the method comprising:
providing a high shear device comprising at least one rotor and at least one complementarily-shaped stator configured to mix a gas with a liquid;
contacting a gas with an organic oil in said high shear device at a temperature above the solidification temperature of the oil, such that said oil maintains a liquid phase, wherein said as is selected from the group consisting of nitrogen, noble gases, and carbon dioxide, thus forming a product, wherein said product is a dispersion comprising a continuous oil phase having gas bubbles dispersed therein, wherein the as bubbles have a mean diameter of less than 50 μm, and wherein contacting the gas with the oil in said high shear device is performed at a temperature no greater than room temperature.

14. A method of producing an oil, the method comprising:
providing a high shear device comprising at least one rotor and at least one complementarily-shaped stator configured to mix a gas with a liquid;
degassing said oil prior to contacting a gas with the oil in said high shear device at temperature above the solidification temperature of the oil, such that said oil maintains a liquid phase, wherein said gas is selected from the group consisting of nitrogen, noble gases, and carbon dioxide, thus forming a product, wherein said product is a dispersion comprising a continuous oil phase having gas bubbles dispersed therein, wherein the gas bubbles have a mean diameter of less than 50 μm.

15. The method of claim 14 wherein the oil degassing is performed under vacuum to extract air from the oil.

* * * * *

UNITED STATES PATENT AND TRADEMARK OFFICE
CERTIFICATE OF CORRECTION

PATENT NO. : 8,940,347 B2
APPLICATION NO. : 13/441389
DATED : January 27, 2015
INVENTOR(S) : Abbas Hassan, Aziz Hassan and Rayford G. Anthony It is certified that error appears in the above-identified patent and that said Letters Patent is hereby corrected as shown below:

In the Claims:

Claim 7, column 15, line 51, manila oil should be changed to --marula oil--.

Claim 9, column 16, line 10; Claim 11, column 16, line 45; Claim 12, column 16, line 58; and Claim 13, column 17, line 5, each occurrence, as should be changed to --gas--.

Claim 14, column 17, line 14, cancel the text "said high shear device at temperature above the solidi-" and insert the following text --said high shear device at a temperature above the solidi- --.

Signed and Sealed this
Twelfth Day of July, 2016

Michelle K. Lee
*Director of the United States Patent and Trademark Office*